(12) United States Patent
Bourdin et al.

(10) Patent No.: US 9,776,020 B2
(45) Date of Patent: Oct. 3, 2017

(54) COMPOSITION COMPRISING AN ALKOXYSILANE AND A MODIFIED STARCH, AND COSMETIC USE THEREOF

(75) Inventors: Claire Bourdin, Levallois-Perret (FR); Isabelle Leguillou, Clichy (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/122,453

(22) PCT Filed: May 28, 2012

(86) PCT No.: PCT/EP2012/059928
§ 371 (c)(1),
(2), (4) Date: Nov. 26, 2013

(87) PCT Pub. No.: WO2012/163869
PCT Pub. Date: Dec. 6, 2012

(65) Prior Publication Data
US 2014/0076346 A1    Mar. 20, 2014

Related U.S. Application Data

(60) Provisional application No. 61/528,624, filed on Aug. 29, 2011.

(30) Foreign Application Priority Data

May 27, 2011    (FR) ..................... 11 54646

(51) Int. Cl.
| A61Q 5/00 | (2006.01) |
| A61Q 5/06 | (2006.01) |
| A61Q 5/12 | (2006.01) |
| A61K 8/58 | (2006.01) |
| A61K 8/73 | (2006.01) |

(52) U.S. Cl.
CPC .............. *A61Q 5/00* (2013.01); *A61K 8/585* (2013.01); *A61K 8/732* (2013.01); *A61Q 5/06* (2013.01); *A61Q 5/12* (2013.01)

(58) Field of Classification Search
None
See application file for complete search history.

(56) References Cited

U.S. PATENT DOCUMENTS

| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,782,790 A | 2/1957 | Hersh et al. |
| 2,961,347 A | 11/1960 | Floyd |
| 3,206,462 A | 9/1965 | McCarty |
| 3,227,615 A | 1/1966 | Korden |
| 3,472,840 A | 10/1969 | Stone et al. |
| 3,589,978 A | 6/1971 | Kamal et al. |
| 3,632,559 A | 1/1972 | Matter et al. |
| 3,874,870 A | 4/1975 | Green et al. |
| 3,910,862 A | 10/1975 | Barabas et al. |
| 3,912,808 A | 10/1975 | Sokol |
| 3,917,817 A | 11/1975 | Vanlerberghe et al. |
| 3,929,990 A | 12/1975 | Green et al. |
| 3,966,904 A | 6/1976 | Green et al. |
| 3,986,825 A | 10/1976 | Sokol |
| 4,001,432 A | 1/1977 | Green et al. |
| 4,005,193 A | 1/1977 | Green et al. |
| 4,013,787 A | 3/1977 | Varlerberghe et al. |
| 4,017,460 A | 4/1977 | Tessler |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,008 A | 5/1977 | Sokol |
| 4,027,020 A | 5/1977 | Green et al. |
| 4,031,307 A | 6/1977 | DeMartino et al. |
| 4,075,136 A | 2/1978 | Schaper |
| 4,131,576 A | 12/1978 | Iovine et al. |
| 4,137,180 A | 1/1979 | Naik et al. |
| 4,165,367 A | 8/1979 | Chakrabarti |
| 4,166,894 A | 9/1979 | Schaper |
| 4,172,887 A | 10/1979 | Vanlerberghe et al. |
| 4,185,087 A | 1/1980 | Morlino |
| 4,189,468 A | 2/1980 | Vanlerberghe et al. |
| 4,197,865 A | 4/1980 | Jacquet et al. |

(Continued)

FOREIGN PATENT DOCUMENTS

| CA | 1069522 A1 | 1/1980 |
| EP | 0080976 A1 | 6/1983 |

(Continued)

OTHER PUBLICATIONS

International Search Report for PCT/EP2012/059926.
Dowing, Donald T., et al., "Essential Fatty Acids and Epidermal Integrity," Dowing in Arch. Dermatol, vol. 123, 1987, pp. 1381-1384.
Todd, Charles, et al., "Volatile Silicone Fluids for Cosmetic Formulations," Cosmetics and Toiletries, vol. 91, Jan. 1976, pp. 27-32.
International Search Report for co-pending application PCT/EP2012/059928.

(Continued)

*Primary Examiner* — Jyothsna Venkat
(74) *Attorney, Agent, or Firm* — The Marbury Law Group, PLLC

(57) ABSTRACT

The invention relates to a composition, especially a cosmetic composition, comprising: (i) one or more alkoxysilanes, and (ii) one or more starches modified with an acid or an acid derivative. The invention also relates to a cosmetic process for treating keratin materials with this composition, and also to the use of this composition for caring for and/or shaping keratin materials.

3 Claims, No Drawings

(56) References Cited

U.S. PATENT DOCUMENTS

| | | |
|---|---|---|
| 4,217,914 A | 8/1980 | Jacquet et al. |
| 4,223,009 A | 9/1980 | Chakrabarti |
| 4,277,581 A | 7/1981 | Vanlerberghe et al. |
| 4,348,202 A | 9/1982 | Grollier et al. |
| 4,349,532 A | 9/1982 | Vanlergerghe et al. |
| 4,381,919 A | 5/1983 | Jacquet et al. |
| 4,422,853 A | 12/1983 | Jacquet et al. |
| 4,579,732 A | 4/1986 | Grollier et al. |
| 4,591,610 A | 5/1986 | Grollier |
| 4,608,250 A | 8/1986 | Jacquet et al. |
| 4,693,935 A | 9/1987 | Mazurek |
| 4,728,571 A | 3/1988 | Clemens et al. |
| 4,761,273 A | 8/1988 | Grollier et al. |
| 4,777,040 A | 10/1988 | Grollier et al. |
| 4,874,554 A | 10/1989 | Lange et al. |
| 4,948,579 A | 8/1990 | Jacquet et al. |
| 4,957,732 A | 9/1990 | Grollier et al. |
| 4,970,066 A | 11/1990 | Grollier et al. |
| 4,972,037 A | 11/1990 | Garbe et al. |
| 5,196,189 A | 3/1993 | Jacquet et al. |
| 5,455,340 A | 10/1995 | Bernard et al. |
| 5,618,523 A | 4/1997 | Zysman et al. |
| 5,773,611 A | 6/1998 | Zysman et al. |
| 2003/0152542 A1* | 8/2003 | Decoster et al. .......... 424/70.12 |
| 2005/0196368 A1* | 9/2005 | Laurent et al. ............. 424/70.2 |
| 2005/0208005 A1 | 9/2005 | Giroud |
| 2006/0110351 A1 | 5/2006 | Koehler et al. |
| 2007/0104672 A1 | 5/2007 | Decoster et al. |
| 2007/0253921 A1 | 11/2007 | Vic et al. |
| 2007/0275927 A1 | 11/2007 | Philippe |
| 2009/0291058 A1* | 11/2009 | Woodland ................ A61K 8/36 424/70.28 |
| 2010/0254932 A1* | 10/2010 | Benabdillah et al. ... 424/70.122 |

FOREIGN PATENT DOCUMENTS

| | | |
|---|---|---|
| EP | 0095238 A2 | 11/1983 |
| EP | 0122324 A1 | 10/1984 |
| EP | 0159628 A1 | 10/1985 |
| EP | 0186507 A2 | 7/1986 |
| EP | 0342834 A2 | 11/1989 |
| EP | 0412704 A2 | 2/1991 |
| EP | 0412707 A1 | 2/1991 |
| EP | 0530974 A1 | 3/1993 |
| EP | 0582152 A2 | 2/1994 |
| EP | 0640105 A1 | 3/1995 |
| EP | 1767189 A2 | 3/2007 |
| EP | 1795180 A1 | 6/2007 |
| EP | 1847252 A2 | 10/2007 |
| EP | 2213334 * | 8/2010 |
| FR | 1492597 A | 8/1967 |
| FR | 1583363 A | 10/1969 |
| FR | 2077143 A | 10/1971 |
| FR | 2080759 A | 11/1971 |
| FR | 2162025 A1 | 7/1973 |
| FR | 2190406 A2 | 2/1974 |
| FR | 2252840 A1 | 6/1975 |
| FR | 2270846 A1 | 12/1975 |
| FR | 2280361 A2 | 2/1976 |
| FR | 2316271 A1 | 1/1977 |
| FR | 2320330 A1 | 3/1977 |
| FR | 2336434 A1 | 7/1977 |
| FR | 2368508 A2 | 5/1978 |
| FR | 2393573 A1 | 1/1979 |
| FR | 2413907 A1 | 8/1979 |
| FR | 2505348 A1 | 11/1982 |
| FR | 2542997 A1 | 9/1984 |
| FR | 2589476 A1 | 5/1987 |
| FR | 2673179 A1 | 8/1992 |
| FR | 2783164 A1 | 3/2000 |
| FR | 2926984 A1 | 8/2009 |
| GB | 1331819 A | 9/1973 |
| GB | 1546809 A | 12/1976 |
| WO | 93/23009 A1 | 11/1993 |
| WO | 93/23446 A2 | 11/1993 |
| WO | 95/00578 A1 | 1/1995 |
| WO | 2012163868 A2 | 6/2012 |

OTHER PUBLICATIONS

International Search Report for counterpart foreign Application No. PCT/EP2012/059928, mailed Dec. 13, 2012.

Non-Final Office Action for co-pending U.S. Appl. No. 14/122,470, mailed Apr. 24, 2015.

Final Office Action for co-pending U.S. Appl. No. 14/122,470, mailed Oct. 22, 2015.

Non-Final Office Action for co-pending U.S. Appl. No. 14/122,470, mailed Aug. 11, 2016.

* cited by examiner

COMPOSITION COMPRISING AN ALKOXYSILANE AND A MODIFIED STARCH, AND COSMETIC USE THEREOF

CROSS REFERENCE TO RELATED APPLICATIONS

This is a national stage application of PCT/EP2012/059928, filed internationally on May 28, 2012, which claims priority to U.S. Provisional Application No. 61/528,624, filed on Aug. 29, 2011, as well as French Application No. FR 1154646, filed May 27, 2011, all of which are incorporated herein by their entireties.

The present invention relates to a composition, especially a cosmetic composition, containing at least one alkoxysilane and at least one starch modified with an acid or an acid derivative.

Keratin fibres may suffer attack of diverse origins, for instance mechanical attack (disentangling or brushing), or chemical attack (dyeing or permanent waving). This attack has an impact on the qualities of the fibre and will lead to difficult disentangling at the time of washing the hair, and to a non-smooth, dry and uneven surface when the hair is dry. The hair is difficult to style and lacks softness.

The conditioning compositions that are currently proposed comprise essentially cationic surfactants, fatty substances, silicones and cationic polymers. They make it possible to facilitate disentangling by softening the keratin fibre and provide sheen, softness, and uniformity to dried hair. However, these effects do not withstand shampooing, and the application of these compositions is essential at each washing step in order to treat and facilitate the disentangling of the hair.

Moreover, it is found that consumers are increasingly in search of care compositions that are not only capable of appropriately conditioning the hair, but also capable of affording satisfactory styling effects.

In particular, people with fine or curly hair are generally in search of care products that afford styling effects that give mass, body and volume to fine hair and curl definition to curly hair.

It has already been proposed especially in FR 2 783 164 to use alkoxysilanes to give the hair styling properties. However, aminosilane-based compositions have problems of stability on storage and also incompatibilities with components widely used in cosmetics such as certain classes of surfactants and of conditioning agents. Consequently, compositions of this type are difficult to thicken.

Furthermore, the results obtained are not completely satisfactory either as regards the cosmetic properties themselves or their durability.

There thus exists a need to have available more effective conditioning and styling compositions.

The Applicant Company has discovered, surprisingly, that compositions comprising at least one ionic starch and at least one alkoxysilane make it possible to solve the problems raised above.

More specifically, one subject of the invention is a composition, especially a cosmetic composition comprising:
(i) one or more alkoxysilanes, and
(ii) one or more starches modified with an acid or an acid derivative.

Such a composition shows satisfactory thickening and furthermore is stable over time. It is easy to distribute over the hair, easy to remove with water and leads to shiny, smooth, soft hair that is easy to disentangle. The composition affords densification to the head of hair (gives the impression of a larger number of hairs), body, volume and ease of shaping, in particular for fine hair. Finally, the compositions according to the invention also make it possible to give curly hair styling effects, especially in terms of curl definition and control.

The styling and cosmetic properties last over time, even after shampooing several times.

A further subject of the invention is a method for the nontherapeutic cosmetic treatment of keratin materials, in particular the hair, comprising the application, to said materials, of a composition as described above.

A subject of the invention is also the use of a composition according to the invention for caring for and shaping keratin materials, especially keratin fibres and in particular human keratin fibres such as the hair.

The composition according to the invention comprises one or more alkoxysilanes.

The alkoxysilanes present in the composition according to the invention are preferably chosen from organosilanes comprising one, two or three silicon atoms, preferably one or two silicon atoms.

The alkoxysilanes present in the composition according to the invention may comprise two or more hydrolysable or hydroxyl groups per molecule. The hydrolysable groups are preferably alkoxy, aryloxy or halogen groups. They may optionally comprise other chemical functions, such as salified or non-salified amine, salified or non-salified carboxylic acid, salified or non-salified sulfonic acid, salified or non-salified phosphoric acid, salified or non-salified sulfuric acid, and aldehyde, polyalcohol or polyether functions.

Preferably, the alkoxysilanes of the invention comprise one or more amine or aldehyde functions.

Even more preferably, the alkoxysilanes of the invention comprise one or more amine functions.

When the alkoxysilane present in the composition according to the invention comprises one or more amine functions, they are preferably primary amines (—NH2) and/or secondary amines (—NHR).

According to one particular embodiment, the alkoxysilane(s) present in the composition according to the invention are chosen from the compounds of formula (I):

in which:
$R_4$ represents a halogen or a group $OR_a$ or $R_{1a}$;
$R_5$ represents a halogen or a group $OR_b$ or $R_{2a}$;
$R_6$ represents a halogen or a group Oft or $R_{3a}$;
$R_1$ and $R_2$ represent, independently of each other, a hydrogen atom, a saturated or unsaturated, linear or branched hydrocarbon-based group, optionally substituted with an amine function, which itself may bear a substitution with a saturated or unsaturated, linear or branched hydrocarbon-based group, possibly bearing an amine function, preferably $R_1$ or $R_2$ necessarily denoting a hydrogen atom,
$R_3$, $R_a$, $R_b$, $R_c$, $R_{1a}$, $R_{2a}$ and $R_{3a}$ represent, independently of each other, a saturated or unsaturated, linear or branched hydrocarbon-based group, optionally bearing additional chemical groups such as acid or amine groups, $R_a$, $R_b$ and $R_c$ also possibly denoting hydrogen, and at least two of the groups $R_4$, $R_5$ and $R_6$ being different from the groups $R_{1a}$, $R_{2a}$ and $R_{3a}$. Preferably, at least two of the groups $R_a$, $R_b$ and $R_c$ are other than hydrogen.

Preferably, the groups $R_1$, $R_2$, $R_a$, $R_{1a}$, $R_{2a}$, $R_{3a}$, $R_b$ and $R_c$ are chosen from $C_1$-$C_{12}$ alkyl, $C_5$-$C_{14}$ aryl, ($C_1$-$C_8$)alkyl($C_5$-$C_{14}$)aryl and ($C_5$-$C_{14}$)aryl($C_1$-$C_8$)alkyl radicals.

Preferably, the group $R_3$ is chosen from $C_1$-$C_{12}$ alkylene radicals, optionally substituted with an amino, $C_5$-$C_{14}$ arylene, ($C_1$-$C_8$)alkylene($C_5$-$C_{14}$)arylene or ($C_5$-$C_{14}$)arylene($C_1$-$C_8$)alkylene group.

According to one particular embodiment, the alkoxysilane(s) corresponding to formula (I) are preferably 3-aminopropyltriethoxysilane, 3-aminopropylmethyldiethoxysilane, N-(2-aminoethyl)-3-aminopropyltriethoxysilane and 3-(2-aminoethylamino)propylmethyldiethoxysilane.

According to another particular embodiment, the alkoxysilane(s) used according to the invention are chosen from the compounds of formula (II):

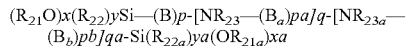

in which: $R_{21}$, $R_{22}$, $R_{21a}$ and $R_{22a}$ represent, independently of each other, a saturated or unsaturated, linear or branched hydrocarbon-based chain, optionally containing one or more heteroatoms, optionally interrupted or substituted with one or more groups chosen from ether, ester, amine, amide, carboxyl, hydroxyl and carbonyl groups, x is an integer ranging from 1 to 3, y=3−x, xa is an integer ranging from 1 to 3, ya=3−xa, p=0 or 1, pa=0 or 1, pb=0 or 1, q=0 or 1, qa=0 or 1, it being understood that at least q or qa is other than zero, B, $B_a$ and $B_b$ each independently represent a linear or branched divalent $C_1$-$C_{20}$ alkylene radical.

$R_{23}$ and $R_{23a}$ each independently represent a hydrogen atom or a saturated or unsaturated, linear or branched hydrocarbon-based chain, optionally containing one or more heteroatoms, optionally interrupted or substituted with one or more ether, $C_1$-$C_{20}$ alcohol ester, amine, carboxyl, $C_6$-$C_{30}$ aryl, hydroxyl or carbonyl groups, or a heterocyclic or non-heterocyclic aromatic ring, optionally substituted with one or more $C_1$-$C_{20}$ alcohol ester, amine, amide, carboxyl, hydroxyl, carbonyl or acyl groups.

Preferably, $R_{23}$ and $R_{23a}$ represent a hydrogen atom.

As explained previously, $R_{21}$, $R_{22}$, $R_{21a}$ and $R_{22a}$ each independently represent a hydrocarbon-based chain. The term "hydrocarbon-based chain" preferably means a chain comprising from 1 to 30 and preferably 1 to 10 carbon atoms.

Preferably, $R_{21}$=$R_{21a}$; $R_{22}$=$R_{22a}$; x=xa; y=ya; p=pa; B=$B_a$; q=1 and qa=0.

The alkoxysilane(s) of formula (II) may also have the following characteristics, taken alone or in combination:
$R_{21}$, $R_{22}$, $R_{21a}$ and $R_{22a}$, which may be identical or different, represent a $C_1$-$C_4$ alkyl,
p=pa=1;
B and $B_a$, which may be identical or different, represent a linear $C_1$-$C_4$ alkylene.

For example, the alkoxysilane(s) are chosen from bis[3-(triethoxysilyl)propyl]amine of formula $(CH_3CH_2O)_3$—Si$(CH_2)_3NH(CH_2)_3Si(OCH_2CH_3)_3$ sold by the company Fluorochem, bis[trimethoxysilylpropyl]amine of formula $(CH_3O)_3$—Si$(CH_2)_3NH(CH_2)_3Si(OCH_3)_3$ sold by the company Gelest, bis[methyldiethoxysilylpropyl]amine of formula $(CH_3CH_2O)_2CH_3Si(CH_2)_3NH(CH_2)_3SiCH_3(OCH_2CH_3)_2$ sold by the company Gelest, and bis[3-trimethoxysilylpropyl]ethylenediamine of formula $(CH_3O)_3Si(CH_2)_3NH(CH)_2NH(CH_2)_3Si(OCH_3)_3$ sold by the company Gelest. Among these compounds, bis[3-(triethoxysilyl)propyl]amine and bis[methyldiethoxysilylpropyl]amine are preferred.

According to another embodiment of the invention, the alkoxysilane(s) are chosen from the compounds of formula (III):

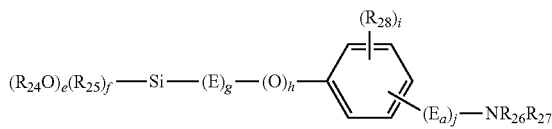

in which:
$R_{24}$ and $R_{25}$ represent, independently of each other, a saturated or unsaturated, linear or branched hydrocarbon-based chain, optionally containing one or more heteroatoms, optionally interrupted or substituted with one or more groups chosen from ether, ester, amine, amide, carboxyl, hydroxyl and carbonyl groups,
e=2 or 3;
f=3−e;
g=0 or 1;
j=0 or 1;
E and $E_a$ each independently represent a linear or branched divalent $C_1$-$C_{20}$ alkylene radical,
$R_{26}$ and $R_{27}$ each independently represent a hydrogen atom or a saturated or unsaturated, linear or branched hydrocarbon-based chain, optionally containing one or more heteroatoms, optionally interrupted or substituted with one or more ether, $C_1$-$C_{20}$ alcohol ester, amine, carboxyl, alkoxysilane, $C_6$-$C_{30}$ aryl, hydroxyl or carbonyl groups, or a heterocyclic or non-heterocyclic aromatic ring, optionally substituted with one or more $C_1$-$C_{20}$ alcohol ester, amine, amide, carboxyl, alkoxysilane, hydroxyl, carbonyl or acyl groups,
i is an integer ranging from 0 to 4,
h is 0 or 1,
the group(s) $R_{28}$ each independently represent a hydrogen atom or a saturated or unsaturated, linear or branched, preferably $C_1$-$C_{10}$ hydrocarbon-based chain, optionally containing one or more heteroatoms, optionally interrupted or substituted with one or more ether, $C_1$-$C_{20}$ alcohol ester, amine, carboxyl, $C_6$-$C_{30}$ aryl, hydroxyl or carbonyl groups, or a heterocyclic or non-heterocyclic aromatic ring, optionally substituted with one or more $C_1$-$C_{20}$ alcohol ester, amine, amide, carboxyl, hydroxyl, carbonyl or acyl groups.

As explained previously, $R_{24}$ and $R_{25}$ each independently represent a hydrocarbon-based chain. The term "hydrocarbon-based chain" preferably means a chain comprising from 1 to 30 and preferably 1 to 10 carbon atoms.

Similarly, $R_{26}$ or $R_{27}$ may represent a hydrocarbon-based chain. In this case, it preferably means a chain comprising from 1 to 30 and preferably 1 to 10 carbon atoms.

Preferably, the aromatic ring comprises from 6 to 30 carbon atoms. Even more preferentially, it denotes an optionally substituted phenyl radical.

The alkoxysilane(s) of formula (III) may have the following characteristics, taken alone or in combination:
$R_{24}$ is a $C_1$-$C_4$ alkyl,
e=3, g=j=1; i=h=0, $R_{26}$ and $R_{27}$ independently represent hydrogen or a group chosen from $C_1$-$C_4$ alkyl, $C_1$-$C_4$ hydroxyalkyl and $C_1$-$C_4$ aminoalkyl groups.

Preferably, $R_{26}$ or $R_{27}$ denote a hydrogen atom.

In particular, the alkoxysilane(s) of formula (III) may be chosen from:

3-(m-aminophenoxy)propyltrimethoxysilane, of formula:

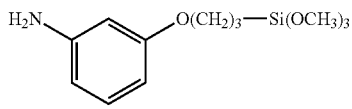

p-aminophenyltrimethoxysilane, of formula:

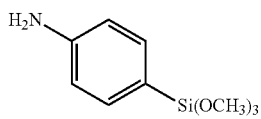

N-(2-aminoethylaminomethyl)phenethyltrimethoxysilane, of formula:

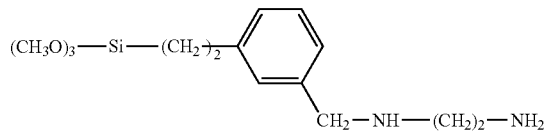

More preferentially, the alkoxysilane(s) that may be used in the compositions according to the present invention correspond to formula (IV):

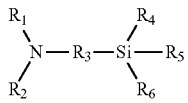

(IV)

in which:

$R_1$ and $R_2$, independently of each other, are chosen from hydrogen and ethyl, propyl and aminoethyl groups;

$R_3$ is chosen from ethyl, propyl and methylphenethyl groups;

$R_4$, $R_5$ and $R_6$, independently of each other, are chosen from methyl, methoxy and ethoxy groups.

In one variant of the invention, the alkoxysilanes of the invention comprise one or more primary or secondary amine functions.

Preferably, the alkoxysilanes of the invention are chosen from the compounds of formulae (I), (III) and (IV) and more particularly the following compounds: 3-aminopropyltriethoxysilane (APTES), 3-aminoethyltriethoxysilane (AETES), 3-aminopropylmethyldiethoxysilane, N-(2-aminoethyl)-3-aminopropyltriethoxysilane and N-(2-aminoethylaminomethyl)phenethyltrimethoxysilane of formula:

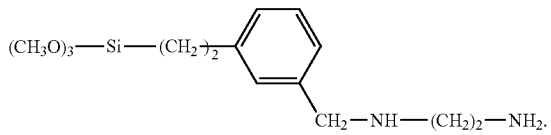

More particularly, the alkoxysilanes of the invention are chosen from the compounds of formula (I), especially 3-aminopropyltriethoxysilane (APTES), 3-aminoethyltriethoxysilane (AETES), 3-aminopropylmethyldiethoxysilane and N-(2-aminoethyl)-3-aminopropyltriethoxysilane and preferably the alkoxysilane is 3-aminopropyltriethoxysilane (APTES).

The alkoxysilane(s) may be present in the cosmetic composition according to the invention in a content ranging from 0.05% to 20%, in particular from 0.1% to 10%, preferably from 0.2% to 5%, by weight relative to the total weight of the composition.

The composition according to the invention comprises one or more starches modified with an acid or an acid derivative.

The starches that may be used in the present invention are more particularly macromolecules in the form of polymers formed from elemental units that are anhydroglucose units. The number of these units and their assembly make it possible to distinguish amylose (linear polymer) and amylopectin (branched polymer). The relative proportions of amylose and of amylopectin, and their degree of polymerization, vary as a function of the plant origin of the starches.

The starch molecules used in the present invention may originate from a plant source such as cereals, tubers, roots, legumes and fruit. Thus, the starch(es) may originate from a plant source chosen from corn, pea, potato, sweet potato, banana, barley, wheat, rice, oat, sago, tapioca and sorghum. The starch is preferably derived from potato.

It is also possible to use the starch hydrolysates mentioned above.

Starches are generally in the form of a white powder, which is insoluble in cold water, whose elemental particle size ranges from 3 to 100 microns.

The starches used in the composition of the invention may be chemically modified via one or more of the following reactions: pregelatinization, oxidation, crosslinking, esterification, heat treatments.

More particularly, these reactions may be performed in the following manner:
  pregelatinization by splitting the starch granules (for example drying and cooking in a drying drum);
  oxidation with strong oxidizing agents, leading to the introduction of carboxyl groups into the starch molecule and to depolymerization of the starch molecule (for example by treating an aqueous starch solution with sodium hypochlorite);
  crosslinking with functional agents capable of reacting with the hydroxyl groups of the starch molecules, which will thus bond together (for example with glyceryl and/or phosphate groups);
  esterification in alkaline medium for the grafting of functional groups, especially $C_1$-$C_6$ acyl (acetyl), $C_1$-$C_6$ hydroxyalkyl (hydroxyethyl or hydroxypropyl) and carboxyalkyl.

The acids or acid derivatives may be mineral or organic acids or acid derivatives. The term "derivatives" means salts of mineral or organic acids, organic acid chlorides, organic acid anhydrides, organic acid esters or mineral oxychlorides.

Monostarch phosphates (of the type Am—O—PO—(OX)$_2$), distarch phosphates (of the type Am—O—PO—(OX)—O—Am) or even tristarch phosphates (of the type Am—O—PO—(O—Am)$_2$) or mixtures thereof may especially be obtained by crosslinking with phosphorus compounds.

X especially denotes alkali metals (for example sodium or potassium), alkaline-earth metals (for example calcium or magnesium), ammonium salts, amine salts, for instance those of monoethanolamine, diethanolamine, triethanolamine, 3-amino-1,2-propanediol, or ammonium salts derived from basic amino acids such as lysine, arginine, sarcosine, ornithine or citrulline.

The phosphorus compounds may be, for example, sodium tripolyphosphate, sodium orthophosphate, phosphorus oxychloride or sodium trimetaphosphate.

Starch phosphates, in particular hydroxypropyl starch phosphates, or compounds rich in starch phosphate and in particular in hydroxypropyl starch phosphate may thus be used, for instance the products sold under the references Prejel VA-70-T AGGL (gelatinized hydroxypropyl cassava distarch phosphate), Prejel TK1 (gelatinized cassava distarch phosphate) and Prejel 200 (gelatinized acetyl cassava distarch phosphate) by the company Avebe, or Structure Zea from National Starch (gelatinized hydroxypropyl corn distarch phosphate).

When the starches are chemically modified via an esterification reaction, carboxyalkyl starches as indicated previously are obtained.

The carboxyalkyl starches are preferably carboxy($C_1$-$C_4$) alkyl starches and salts thereof, and more particularly carboxymethyl starches and salts thereof.

The salts are especially salts of alkali metals or alkaline-earth metals such as Na, K ½, Li, $NH_4$, or salts of a quaternary ammonium or of an organic amine such as monoethanolamine, diethanolamine or triethanolamine.

Carboxyalkyl starches are obtained by grafting carboxyalkyl groups onto one or more alcohol functions of starch, especially by reaction of starch and of sodium monochloroacetate in alkaline medium.

The carboxyalkyl groups are generally attached via an ether function, more particularly to carbon 1.

The degree of substitution preferably ranges from 0.1 to 1 and more particularly from 0.15 to 0.5. The degree of substitution is defined according to the present invention as being the mean number of hydroxyl groups substituted with an ester or ether group (in the present case ether for the carboxymethyl starches) per monosaccharide unit of the polysaccharide.

The carboxyalkyl starches preferably comprise units having the following formula:

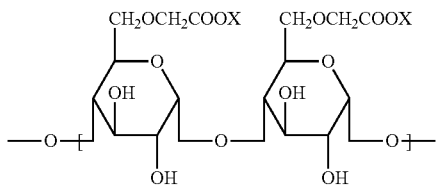

X denotes a hydrogen atom, an alkali metal or alkaline-earth metal such as Na, K ½, Li or $NH_4$, a quaternary ammonium or an organic amine. Preferably, X denotes an ion $Na^+$.

The carboxyalkyl starches that may be used according to the present invention are preferably non-pregelatinized carboxyalkyl starches.

The carboxyalkyl starches that may be used according to the present invention are preferably partially or totally crosslinked carboxyalkyl starches.

The carboxyalkyl starches that may be used according to the present invention are preferably sodium salts of carboxyalkyl starches, in particular a sodium salt of potato carboxymethyl starch, sold especially under the name Primojel by the company DMV International. More than 95% of the particles of this starch have a diameter of less than 100 microns and more particularly less than 65 microns.

Starch acetates or acetylated starches may also be used in the invention, the acetylation possibly being performed especially with acetic anhydride or with vinyl acetate. A starch acetate that may be mentioned is the product Perfectamyl AC sold by the company Avebe.

According to the invention, it is also possible to use amphoteric starches, these amphoteric starches containing one or more anionic groups and one or more cationic groups. The anionic and cationic groups may be linked to the same reactive site of the starch molecule or to different reactive sites; they are preferably linked to the same reactive site. The anionic groups may be of carboxylic, phosphate or sulfate type, preferably carboxylic. The cationic groups may be of primary, secondary, tertiary or quaternary amine type.

The amphoteric starches are especially chosen from the compounds having the following formulae:

  (V)

  (VI)

  (VII)

  (VIII)

in which formulae:
St-O represents a starch molecule,
R, which may be identical or different, represents a hydrogen atom or a methyl radical,
R', which may be identical or different, represents a hydrogen atom, a methyl radical or a —COOH group,
n is an integer equal to 2 or 3,
M, which may be identical or different, denotes a hydrogen atom, an alkali metal or alkaline-earth metal such as Na, K, Li or $NH_4$, a quaternary ammonium or an organic amine,
R" represents a hydrogen atom or an alkyl radical containing from 1 to 18 carbon atoms.

These compounds are especially described in U.S. Pat. No. 5,455,340 and U.S. Pat. No. 4,017,460.

The starches of formula (V) or (VI) are particularly used as amphoteric starches. Starches modified with 2-chloroethylaminodipropionic acid are more particularly used, i.e. starches of formula (V) or (VI) in which R, R', R" and M represent a hydrogen atom and n is equal to 2. Mention may be made in particular of the potato starch modified with 2-chloroethylaminodipropionic acid neutralized with sodium hydroxide, sold under the reference Structure Solanace by the company National Starch.

Preferably, one or more starches chosen from starch phosphates and starch acetates will be used.

According to the invention, the starch(es) modified with an acid derivative may represent from 0.01% to 10% by weight, preferably from 0.1% to 10% by weight and more particularly from 0.5% to 5% by weight relative to the total weight of the composition.

The weight ratio of the amount of starch modified with an acid derivative to the amount of alkoxysilane ranges from 0.01 to 20, preferably from 0.05 to 10 and better still from 0.1 to 5.

The composition according to the invention may comprise water, one or more organic solvents or a mixture of water and one or more organic solvents, the organic solvents preferably being selected from $C_1$-$C_4$ lower alcohols such as ethanol, isopropanol, tert-butanol or n-butanol; polyols such as glycerol, propylene glycol, dipropylene glycol and polyethylene glycols; and mixtures thereof.

In the composition according to the invention, the water may be present in a content ranging from 10% to 95% by weight and preferably ranging from 20% to 95% by weight relative to the total weight of the composition.

The composition according to the invention may also comprise one or more thickeners other than the modified starches as described previously.

The thickener(s) may be selected from fatty acid amides obtained from a $C_{10}$-$C_{30}$ carboxylic acid (coconut acid monoisopropanolamide, diethanolamide or monoethanolamide, oxyethylenated alkyl ether carboxylic acid monoethanolamide), cellulose-based thickeners (hydroxyethyl cellulose, hydroxypropyl cellulose, carboxymethyl cellulose), guar gum and nonionic derivatives thereof (hydroxypropyl guar), gums of microbial origin (xanthan gum, scleroglucan gum), nonionic starches and associative polymers.

The associative polymer(s) that may be used according to the invention are water-soluble polymers that are capable, in aqueous medium, of reversibly combining with each other or with other molecules.

Their chemical structure comprises hydrophilic zones, and hydrophobic zones characterized by at least one fatty chain containing preferably from 10 to 30 carbon atoms.

The associative polymer(s) that may be used according to the invention and that are different from the acrylic thickening polymers may be of anionic, cationic, amphoteric or nonionic type, such as the polymers sold under the names Elfacos T210 or T212 by the company Akzo.

Among all the additional thickeners mentioned, the thickener(s) are preferably chosen from cellulose-based thickeners.

When they are present, the composition preferably comprises from 0.1% to 20% by weight, and better still from 0.2% to 10% by weight, of additional thickener(s), relative to the total weight of the composition.

The composition according to the invention may also comprise one or more conditioning agents.

According to the present invention, the term "conditioning agent" denotes any compound that can improve the cosmetic properties of the hair, in particular the softness, disentangling, feel and static electricity.

The conditioning agent is preferably selected from the group comprising cationic polymers, cationic surfactants, silicones such as organosiloxanes, linear or branched $C_8$-$C_{30}$ hydrocarbons, linear or branched $C_8$-$C_{30}$ fatty alcohols, esters of $C_8$-$C_{30}$ fatty acid and $C_1$-$C_{30}$ alcohol, and especially esters of $C_8$-$C_{30}$ fatty acid and $C_8$-$C_{30}$ fatty alcohol, esters of $C_1$-$C_7$ acid or diacid and $C_8$-$C_{30}$ fatty alcohol, ceramides or ceramide analogues, and mixtures of these compounds.

The term "cationic polymer" means a polymer that is positively charged when it is contained in the composition according to the invention. This polymer may bear one or more positive permanent charges or may contain one or more cationizable functions in the composition according to the invention.

The cationic polymer(s) that may be used as conditioning agents according to the present invention are preferably selected from polymers comprising primary, secondary, tertiary and/or quaternary amine groups forming part of the polymer chain or directly attached thereto, and having a molecular weight of between 500 and about 5 000 000 and preferably between 1000 and 3 000 000.

Among the cationic polymers that may be mentioned more particularly are polymers of the polyamine, polyaminoamide and polyquaternary ammonium type. These are known products. They are described, for example, in French Patents 2 505 348 and 2 542 997.

Among these polymers, mention may be made of:

(1) homopolymers or copolymers derived from acrylic or methacrylic esters or amides and comprising at least one of the units of the following formulae:

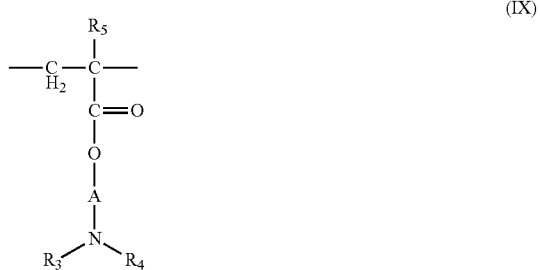

(IX)

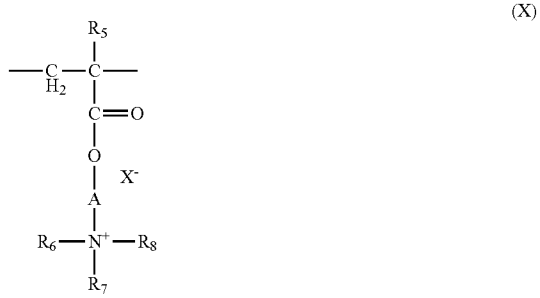

(X)

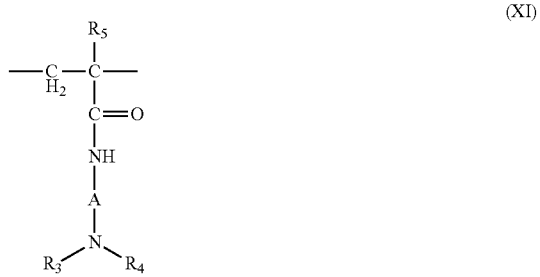

(XI)

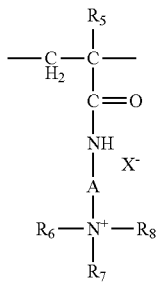

(XII)

in which:

$R_3$ and $R_4$, which are identical or different, represent a hydrogen atom or an alkyl group having from 1 to 6 carbon atoms, and preferably methyl or ethyl;

$R_5$, which are identical or different, denote a hydrogen atom or a $CH_3$ group;

A, which are identical or different, represent a linear or branched alkyl group having from 1 to 6 carbon atoms, preferably 2 or 3 carbon atoms, or a hydroxyalkyl group having from 1 to 4 carbon atoms;

$R_6$, $R_7$, $R_8$, which are identical or different, represent an alkyl group having from 1 to 18 carbon atoms or a benzyl group, and preferably an alkyl group having from 1 to 6 carbon atoms;

$X^-$ denotes an anion derived from an organic or inorganic acid, such as a methosulfate anion, or a halide such as chloride or bromide.

The copolymers of the family (1) may further contain one or more units deriving from comonomers which may be selected from the family of acrylamides, methacrylamides, diacetone acrylamides, acrylamides and methacrylamides substituted on the nitrogen by lower ($C_1$-$C_4$) alkyls, acrylic acids or methacrylic acids or esters thereof, vinyllactams such as vinylpyrrolidone or vinylcaprolactam, and vinyl esters.

Thus, among these copolymers of the family (1), mention may be made of:
  copolymers of acrylamide and of dimethylaminoethyl methacrylate quaternized with dimethyl sulfate or with a dimethyl halide, such as that sold under the name Hercofloc by the company Hercules,
  copolymers of acrylamide and of methacryloyloxyethyltrimethylammonium chloride, described, for example, in Patent Application EP-A-080 976 and sold under the name Bina Quat P 100 by the company Ciba Geigy,
  the copolymer of acrylamide and of methacryloyloxyethyltrimethylammonium methosulfate sold under the name Reten by the company Hercules,
  quaternized or non-quaternized vinylpyrrolidone/dialkylaminoalkyl acrylate or methacrylate copolymers, such as the products sold under the name Gafquat by the company ISP, such as, for example, Gafquat 734 or Gafquat 755, or alternatively the products known as Copolymer 845, 958 and 937. These polymers are described in detail in French Patents 2 077 143 and 2 393 573,
  dimethylaminoethyl methacrylate/vinylcaprolactam/vinylpyrrolidone terpolymers, such as the product sold under the name Gaffix VC 713 by the company ISP,
  vinylpyrrolidone/methacrylamidopropyldimethylamine copolymers sold in particular under the name Styleze CC 10 by the company ISP,
  quaternized vinylpyrrolidone/dimethylaminopropyl methacrylamide copolymers, such as the product sold under the name Gafquat HS 100 by the company ISP, and
  the crosslinked polymers of methacryloyloxy($C_1$-$C_4$) alkyl tri($C_1$-$C_4$)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with an olefinically unsaturated compound, more particularly methylenebisacrylamide. A crosslinked acrylamide/methacryloyloxyethyltrimethylammonium chloride copolymer (20/80 by weight) in the form of a dispersion containing 50% by weight of said copolymer in mineral oil can be used more particularly. This dispersion is sold under the name Salcare® SC 92 by the company Ciba. A crosslinked methacryloyloxyethyltrimethylammonium chloride homopolymer, for example as a dispersion in mineral oil or in a liquid ester, can also be used. These dispersions are sold under the names Salcare® SC 95 and Salcare® SC 96 by the company Ciba.

(2) Polymers composed of piperazinyl units and of divalent alkylene or hydroxyalkylene groups containing straight or branched chains, optionally interrupted by oxygen, sulfur or nitrogen atoms or by aromatic or heterocyclic rings, and also the oxidation and/or quaternization products of these polymers. Such polymers are especially described in French Patents 2 162 025 and 2 280 361.

(3) Water-soluble polyaminoamides prepared in particular by polycondensation of an acidic compound with a polyamine; these polyaminoamides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyaminoamide; these polyaminoamides can be alkylated or, if they comprise one or more tertiary amine functions, they can be quaternized. Such polymers are especially described in French Patents 2 252 840 and 2 368 508.

(4) Polyaminoamide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl groups contain from 1 to 4 carbon atoms and preferably denote a methyl, ethyl or propyl group, and the alkylene groups contain from 1 to 4 carbon atoms and preferably denote the ethylene group. Such polymers are especially described in French Patent 1 583 363.

Among these derivatives, mention may be made more particularly of the adipic acid/dimethylaminohydroxypropyl/diethylenetriamine polymers sold under the name Cartaretine F, F4 or F8 by the company Sandoz.

(5) The polymers obtained by reaction of a polyalkylene polyamine containing two primary amine groups and at least one secondary amine group with a dicarboxylic acid selected from diglycolic acid and saturated aliphatic dicarboxylic acids having from 3 to 8 carbon atoms. The molar ratio between the polyalkylene polyamine and the dicarboxylic acid is between 0.8:1 and 1.4:1; the polyaminoamide resulting therefrom is reacted with epichlorohydrin in a molar ratio of epichlorohydrin relative to the secondary amine group of the polyaminoamide of between 0.5:1 and 1.8:1. Such polymers are described in particular in U.S. Pat. Nos. 3,227,615 and 2,961,347.

Polymers of this type are sold in particular under the name Hercosett 57 by the company Hercules Inc. or alternatively under the name PD 170 or Delsette 101 by the company Hercules in the case of the adipic acid/epoxypropyl/diethylenetriamine copolymer.

(6) Cyclopolymers of alkyldiallylamine or of dialkyldiallylammonium, such as homopolymers or copolymers comprising, as main constituent of the chain, units corresponding to formula (XIII) or (XIV):

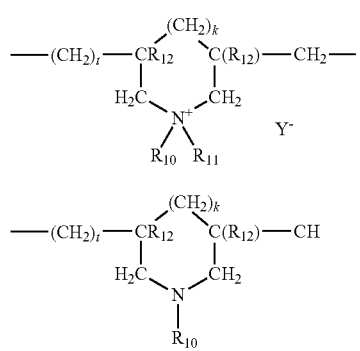

in which formulae: k and t are equal to 0 or 1, the sum k+t being equal to 1; $R_{12}$ denotes a hydrogen atom or a methyl group; $R_{10}$ and $R_{11}$, independently of one another, denote an alkyl group having from 1 to 6 carbon atoms, a hydroxyalkyl group in which the alkyl group has preferably 1 to 5 carbon atoms, a lower ($C_1$-$C_4$) amidoalkyl group, or else $R_{10}$ and $R_{11}$ may, together with the nitrogen atom to which they are attached, denote heterocyclic groups, such as piperidyl or morpholinyl; $Y^-$ is an anion such as bromide, chloride, acetate, borate, citrate, tartrate, bisulfate, bisulfite, sulfate or phosphate. These polymers are especially described in French Patent 2 080 759 and in its Certificate of Addition 2 190 406.

$R_{10}$ and $R_{11}$, independently of one another, preferably denote an alkyl group having from 1 to 4 carbon atoms.

Among the polymers defined above, mention may be made more particularly of the dimethyldiallylammonium chloride homopolymer sold under the name Merquat 100 by the company Nalco (and its homologues of low weight-average molecular weights) and the copolymers of diallyldimethylammonium chloride and of acrylamide, sold under the name Merquat 550.

(7) The quaternary diammonium polymer containing repeating units corresponding to formula (XV):

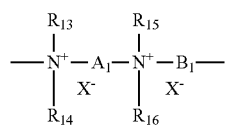

in which formula (XV):

$R_{13}$, $R_{14}$, $R_{15}$ and $R_{16}$, which may be identical or different, represent aliphatic, alicyclic or arylaliphatic groups containing from 1 to 7 carbon atoms or lower ($C_1$-$C_4$) hydroxyalkylaliphatic groups, or alternatively $R_{13}$, $R_{14}$, $R_{15}$ and $R_{16}$, together or separately, constitute, with the nitrogen atoms to which they are attached, heterocycles optionally containing a second heteroatom other than nitrogen, or alternatively $R_{13}$, $R_{14}$, $R_{15}$ and $R_{16}$ represent a linear or branched $C_1$-$C_6$ alkyl group substituted with a nitrile, ester, acyl or amide group or a —CO—O—$R_{17}$-D or —CO—NH—$R_{17}$-D group where $R_{17}$ is an alkylene having from 1 to 10 carbon atoms and D is a quaternary ammonium group;

$A_1$ and $B_1$ represent polymethylene groups containing from 2 to 20 carbon atoms, which may be linear or branched and saturated or unsaturated and may contain, joined to or intercalated in the main chain, one or more aromatic rings, or one or more oxygen or sulfur atoms or sulfoxide, sulfone, disulfide, amino, alkylamino, hydroxyl, quaternary ammonium, ureido, amide or ester groups, and $X^-$ denotes an anion derived from an inorganic or organic acid;

$A_1$, $R_{13}$ and $R_{15}$ may, with the two nitrogen atoms to which they are attached, form a piperazine ring; moreover, if $A_1$ denotes a linear or branched, saturated or unsaturated alkylene or hydroxyalkylene group, $B_1$ may also denote a group —$(CH_2)_n$—CO-D-OC—$(CH_2)_p$— in which:

n and p are integers ranging from 2 to 20 approximately, D denotes:

a) a glycol residue of formula: —O—Z—O—, where Z denotes a linear or branched hydrocarbon-based group or a group corresponding to one of the following formulae:

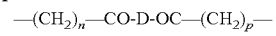

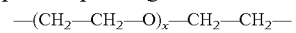

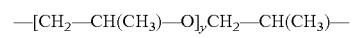

where x and y denote an integer from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH—, where Y denotes a linear or branched hydrocarbon-based group, or else the divalent group —$CH_2$—$CH_{2-S}$—S—$CH_2$—$CH_2$—;

d) an ureylene group of formula: —NH—CO—NH—.

Preferably, $X^-$ is an anion such as chloride or bromide.

These polymers generally have a number-average molecular weight of between 1000 and 100 000.

Polymers of this type are described in particular in French Patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Use may be made more particularly of polymers that are formed from repeating units corresponding to formula (XVI):

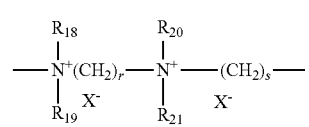

in which: $R_{18}$, $R_{19}$, $R_{20}$ and $R_{21}$, which are identical or different, denote an alkyl or hydroxyalkyl group having from 1 to 4 carbon atoms approximately, r and s are integers ranging from 2 to 20 approximately, and $X^-$ is an anion derived from an inorganic or organic acid.

One particularly preferred compound of formula (XVI) is that for which $R_{18}$, $R_{19}$, $R_{20}$ and $R_{21}$ represent a methyl group and r=3, s=6 and X=Cl, which is called Hexadimethrine chloride according to INCI nomenclature (CTFA).

(8) Polyquaternary ammonium polymers consisting of units of formula (XVII):

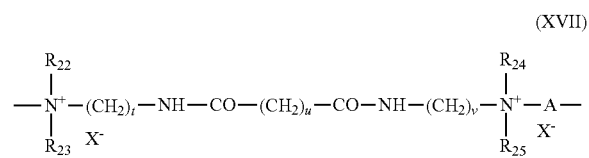

(XVII)

in which formula:

$R_{22}$, $R_{23}$, $R_{24}$ and $R_{25}$, which are identical or different, represent a hydrogen atom or a methyl, ethyl, propyl, β-hydroxyethyl, β-hydroxypropyl or —CH$_2$CH$_2$(OCH$_2$CH$_2$)$_p$OH group, where p is equal to 0 or to an integer between 1 and 6, with the proviso that $R_{22}$, $R_{23}$, $R_{24}$ and $R_{25}$ do not simultaneously represent a hydrogen atom, t and u, which may be identical or different, are integers between 1 and 6, v is equal to 0 or to an integer between 1 and 34, $X^-$ denotes an anion such as a halide, A denotes a dihalide group or preferably represents —CH$_2$—CH$_2$—O—CH$_2$—CH$_2$—.

Such compounds are described especially in Patent Application EP-A-122 324.

Among these, mention may be made, for example, of the products Mirapol® A 15, Mirapol® AD1, Mirapol® AZ1 and Mirapol® 175, sold by the company Miranol.

(9) Quaternary polymers of vinylpyrrolidone and of vinylimidazole, for instance the products sold under the names Luviquat® FC 905, FC 550 and FC 370 by the company BASF.

(10) Cationic polysaccharides, in particular cationic celluloses and derivatives of cationic celluloses, and cationic galactomannan gums.

Among the cationic polysaccharides, mention may be made more particularly of cellulose ether derivatives comprising quaternary ammonium groups, cationic cellulose copolymers or cellulose derivatives grafted with a water-soluble quaternary ammonium monomer and cationic galactomannan gums.

The cellulose ether derivatives comprising quaternary ammonium groups are described in French Patent 1 492 597. These polymers are also defined in the CTFA dictionary as quaternary ammoniums of hydroxyethyl cellulose that have reacted with an epoxide substituted with a trimethylammonium group.

The cationic cellulose copolymers or the cellulose derivatives grafted with a water-soluble quaternary ammonium monomer are described especially in U.S. Pat. No. 4,131,576, such as hydroxyalkyl celluloses, for instance hydroxymethyl, hydroxyethyl or hydroxypropyl celluloses grafted especially with a methacryloylethyltrimethylammonium, methacrylamidopropyltri-methylammonium or dimethyldiallylammonium salt.

The cationic galactomannan gums are described more particularly in U.S. Pat. Nos. 3,589,578 and 4,031,307, in particular guar gums comprising cationic trialkylammonium groups. Use is made, for example, of guar gums modified with a 2,3-epoxypropyltrimethylammonium salt (for example, chloride).

Other cationic polymers that may be used in the context of the invention are cationic proteins or cationic protein hydrolysates, polyalkyleneimines, in particular polyethyleneimines, polymers containing vinylpyridine or vinylpyridinium units, condensates of polyamines and of epichlorohydrin, quaternary polyureylenes and chitin derivatives.

The cationic proteins or protein hydrolysates are, in particular, chemically modified polypeptides bearing quaternary ammonium groups at the end of the chain, or grafted thereon. Their molecular weight may vary, for example, from 1500 to 10 000 and in particular from 2000 to 5000 approximately. Among these compounds, mention may be made especially of:
  collagen hydrolysates bearing triethylammonium groups, such as the products sold under the name Quat-Pro E by the company Maybrook and referred to in the CTFA dictionary as Triethonium Hydrolyzed Collagen Ethosulfate;
  collagen hydrolysates bearing trimethylammonium chloride and trimethylstearylammonium chloride groups, which are sold under the name Quat-Pro S by the company Maybrook and are referred to in the CTFA dictionary as Steartrimonium Hydrolyzed Collagen;
  animal protein hydrolysates bearing trimethylbenzylammonium groups, such as the products sold under the name Crotein BTA by the company Croda and referred to in the CTFA dictionary as Benzyltrimonium hydrolyzed animal protein;
  protein hydrolysates bearing quaternary ammonium groups on the polypeptide chain, said ammonium groups containing at least one alkyl group having from 1 to 18 carbon atoms.

Among these protein hydrolysates, mention may be made, inter alia, of:
  Croquat L, in which the quaternary ammonium groups contain a $C_{12}$ alkyl group;
  Croquat M, in which the quaternary ammonium groups contain $C_{10}$-$C_{18}$ alkyl groups;
  Croquat S, in which the quaternary ammonium groups contain a $C_{18}$ alkyl group;
  Crotein Q, in which the quaternary ammonium groups contain at least one alkyl group having from 1 to 18 carbon atoms.

These various products are sold by the company Croda.

Other quaternized proteins or hydrolysates are, for example, those corresponding to the formula (XVIII):

(XVIII)

in which $X^-$ is an anion of an organic or inorganic acid, A denotes a protein residue derived from collagen protein hydrolysates, $R_{29}$ denotes a lipophilic group containing up to 30 carbon atoms, and $R_{30}$ represents an alkylene group having 1 to 6 carbon atoms. Mention may, for example, be made of the products sold by the company Inolex, under the name Lexein QX 3000, called, in the CTFA dictionary, Cocotrimonium Collagen Hydrolysate.

Mention may also be made of quaternized plant proteins such as wheat, corn or soybean proteins: quaternized wheat proteins that may be mentioned include those sold by the company Croda under the names Hydrotriticum WQ or QM, which in the CTFA dictionary are called Cocodimonium Hydrolysed wheat protein, or Hydrotriticum QL, which in the CTFA dictionary is called Laurdimonium hydrolysed wheat protein, or else Hydrotriticum QS, which in the CTFA dictionary is called Steardimonium hydrolysed wheat protein.

Among all the cationic polymers that may be used in the context of the present invention, it is preferred to use cationic cyclopolymers, such as defined above, in particular the dimethyldiallylammonium chloride homopolymers or copolymers sold under the names Merquat 100, Merquat 550 and Merquat S by the company Nalco, and quaternary vinylpyrrolidone and vinylimidazole polymers, cationic polysaccharides and mixtures thereof.

The conditioning agent(s) that can be used according to the invention may be selected from cationic surfactants.

The term "cationic surfactant" means a surfactant that is positively charged when it is contained in the composition according to the invention. This surfactant may bear one or more positive permanent charges or may contain one or more functions that are cationizable in the composition according to the invention.

The cationic surfactant(s) that may be used as conditioning agents according to the present invention are preferably selected from optionally polyoxyalkylenated primary, secondary or tertiary fatty amines, or the salts thereof, quaternary ammonium salts, and mixtures thereof.

The fatty amines generally comprise at least one $C_8$-$C_{30}$ hydrocarbon-based chain. Among the fatty amines that can be used according to the invention, examples that may be mentioned include stearylamidopropyldimethylamine and distearylamine.

Examples of quaternary ammonium salts that may especially be mentioned include:
those corresponding to the general formula (XIX) below:

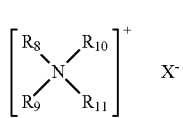

(XIX)

in which the groups $R_8$ to $R_{11}$, which may be identical or different, represent a linear or branched aliphatic group containing from 1 to 30 carbon atoms, or an aromatic group such as aryl or alkylaryl, at least one of the groups $R_8$ to $R_{11}$ denoting a group containing from 8 to 30 carbon atoms, preferably from 12 to 24 carbon atoms. The aliphatic groups may comprise heteroatoms such as, in particular, oxygen, nitrogen, sulfur and halogens. The aliphatic groups are chosen, for example, from $C_{1-30}$ alkyl, $C_{1-30}$ alkoxy, ($C_2$-$C_6$)-polyoxyalkylene, $O_{1-30}$ alkylamide, ($C_{12}$-$C_{22}$)alkylamido($C_2$-$C_6$)alkyl, ($C_{12}$-$C_{22}$)alkylacetate, and $C_{1-30}$ hydroxyalkyl; $X^-$ is an anion chosen from the group of halides, phosphates, acetates, lactates, ($C_1$-$C_4$)alkyl sulfates and ($C_1$-$C_4$)alkyl sulfonates or ($C_1$-$C_4$)alkylaryl sulfonates.

Among the quaternary ammonium salts of formula (XIX), those that are preferred are, on the one hand, tetraalkylammonium salts, for instance dialkyldimethylammonium or alkyltrimethylammonium salts in which the alkyl group contains approximately from 12 to 22 carbon atoms, in particular behenyltrimethylammonium, distearyldimethylammonium, cetyltrimethylammonium or benzyldimethylstearylammonium salts, or, on the other hand, the palmitylamidopropyltrimethylammonium salt, the stearamidopropyltrimethylammonium salt, the stearamidopropyldimethylcetearylammonium salt, or the stearamidopropyldimethyl(myristyl acetate)ammonium salt sold under the name Ceraphyl® 70 by the company Van Dyk. It is particularly preferred to use the chloride salts of these compounds;

quaternary ammonium salts of imidazoline, for instance those of formula (XX) below:

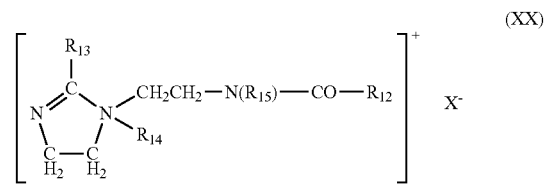

(XX)

in which $R_{12}$ represents an alkenyl or alkyl group containing from 8 to 30 carbon atoms, for example tallow fatty acid derivatives, $R_{13}$ represents a hydrogen atom, a $C_1$-$C_4$ alkyl group or an alkenyl or alkyl group containing from 8 to 30 carbon atoms, $R_{14}$ represents a $C_1$-$C_4$ alkyl group, $R_{15}$ represents a hydrogen atom or a $C_1$-$C_4$ alkyl group, $X^-$ is an anion chosen from the group of halides, phosphates, acetates, lactates, alkyl sulfates, alkyl sulfonates or alkylaryl sulfonates, the alkyl and aryl groups of which preferably comprise, respectively, from 1 to 20 carbon atoms and from 6 to 30 carbon atoms. $R_{12}$ and $R_{13}$ preferably denote a mixture of alkenyl or alkyl groups comprising from 12 to 21 carbon atoms, for example tallow fatty acid derivatives, $R_{14}$ denotes a methyl group, and $R_{15}$ denotes a hydrogen atom. Such a product is sold, for example, under the name Rewoquat® W 75 by the company Rewo;

quaternary di- or triammonium salts of formula (XXI):

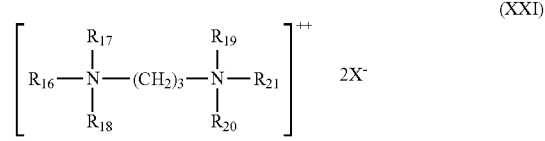

(XXI)

in which $R_{16}$ denotes an alkyl group containing approximately from 16 to 30 carbon atoms, which is optionally hydroxylated and/or interrupted with one or more oxygen atoms, $R_{17}$ is selected from hydrogen or an alkyl group containing from 1 to 4 carbon atoms or the following group:

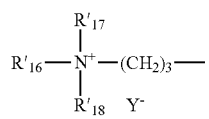

$R'_{16}$, $R'_{17}$, $R'_{18}$, $R_{18}$, $R_{19}$, $R_{20}$ and $R_{21}$, which may be identical or different, are selected from hydrogen or an alkyl group containing from 1 to 4 carbon atoms, and $X^-$ and $Y^-$ are anions in particular selected from the group of halides, acetates, phosphates, nitrates and ($C_1$-$C_6$)alkyl sulfates, in particular methyl sulfate or ethyl sulfate. Such compounds are, for example, Finquat CT-P from the company Finetex (Quaternium-89), Finquat CT from the company Finetex (Quaternium 75) and Condicate CT from the company Innospec Active Chemicals (Quaternium-75);

quaternary ammonium salts containing at least one ester function, such as those of formula (XXII) below:

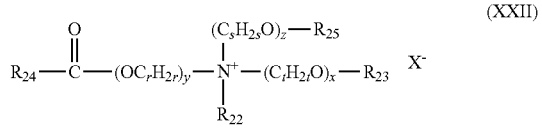
(XXII)

in which:

$R_{22}$ is chosen from $C_1$-$C_6$ alkyl groups and $C_1$-$C_6$ hydroxyalkyl or dihydroxyalkyl groups;

$R_{23}$ is chosen from:

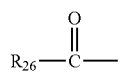

the group
groups $R_{27}$ which are linear or branched, saturated or unsaturated $C_1$-$C_{22}$ hydrocarbon-based groups,
a hydrogen atom,
$R_{25}$ is chosen from:
the group

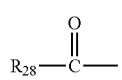

groups $R_{29}$ which are linear or branched, saturated or unsaturated $C_1$-$C_6$ hydrocarbon-based groups,
a hydrogen atom,
$R_{24}$, $R_{26}$ and $R_{28}$, which may be identical or different, are chosen from linear or branched, saturated or unsaturated $C_7$-$C_{21}$ hydrocarbon-based groups;
r, s and t, which may be identical or different, are integers ranging from 2 to 6;
y is an integer ranging from 1 to 10;
x and z, which may be identical or different, are integers ranging from 0 to 10;
$X^-$ is a simple or complex, organic or inorganic anion;
with the proviso that the sum x+y+z is from 1 to 15, that when x is 0, then $R_{23}$ denotes $R_{27}$ and that when z is 0, then $R_{25}$ denotes $R_{29}$.

The alkyl groups $R_{22}$ may be linear or branched, and more particularly linear.

Preferably, $R_{22}$ denotes a methyl, ethyl, hydroxyethyl or dihydroxypropyl group, and more particularly a methyl or ethyl group.

Advantageously, the sum x+y+z is from 1 to 10.

When $R_{23}$ is a hydrocarbon-based group $R_{27}$, it may be long and contain from 12 to 22 carbon atoms, or may be short and contain from 1 to 3 carbon atoms.

When $R_{25}$ is a hydrocarbon-based group $R_{29}$, it preferably contains 1 to 3 carbon atoms.

Advantageously, $R_{24}$, $R_{26}$ and $R_{28}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anion $X^-$ is preferably a halide (chloride, bromide or iodide) or an alkyl sulfate, more particularly methyl sulfate. However, use may be made of methanesulfonate, phosphate, nitrate, tosylate, an anion derived from an organic acid, such as acetate or lactate, or any other anion compatible with the ammonium containing an ester function.

The anion $X^-$ is even more particularly chloride or methyl sulfate.

Use is made more particularly, in the composition according to the invention, of the ammonium salts of formula (XXII) in which:

$R_{22}$ denotes a methyl or ethyl group,
x and y are equal to 1;
z is equal to 0 or 1;
r, s and t are equal to 2;
$R_{23}$ is chosen from:
the group

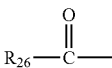

methyl, ethyl or $C_{14}$-$C_{22}$ hydrocarbon-based groups;
a hydrogen atom;
$R_{25}$ is chosen from:
the group

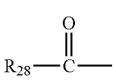

a hydrogen atom;
$R_{24}$, $R_{26}$ and $R_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups.

The hydrocarbon-based groups are advantageously linear.

Mention may be made, for example, of the compounds of formula (XXII) such as the diacyloxyethyldimethylammonium, diacyloxyethylhydroxyethylmethylammonium, monoacyloxyethyldihydroxyethyl-methylammonium, triacyloxyethylmethylammonium and monoacyloxyethylhydroxyethyldimethylammonium salts (chloride or methyl sulfate in particular), and mixtures thereof. The acyl groups preferably contain 14 to 18 carbon atoms and are obtained more particularly from a plant oil such as palm oil or sunflower oil. When the compound contains several acyl groups, these groups may be identical or different.

These products are obtained, for example, by direct esterification of triethanolamine, of triisopropanolamine, of alkyldiethanolamine or of alkyldiisopropanolamine, which are optionally alkoxylated, with $C_{10}$-$C_{30}$ fatty acids or with mixtures of $C_{10}$-$C_{30}$ fatty acids of plant or animal origin, or by transesterification of their methyl esters. This esterification is followed by a quaternization using an alkylating agent such as an alkyl halide (preferably a methyl or ethyl halide), a dialkyl sulfate (preferably a dimethyl or diethyl sulfate), methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company Ceca or Rewoquat® WE 18 by the company Rewo-Witco.

The composition according to the invention may contain, for example, a mixture of quaternary ammonium monoester, diester and triester salts with a weight majority of diester salts.

It is also possible to use the ammonium salts containing at least one ester function that are described in U.S. Pat. No. 4,874,554 and U.S. Pat. No. 4,137,180.

The particularly preferred cationic surfactant(s) that may be used according to the invention are selected from compounds of formula (XIX) or of formula (XXII), methyl($C_9$-$C_{19}$)alkyl($C_{10}$-$C_{20}$)alkylamidoethylimidazolium salts, and stearamidopropyldimethylamine.

Among all the cationic surfactants that may be present in the composition according to the invention, it is preferred to select cetyltrimethylammonium, behenyltrimethylammonium, di(palmitoyloxyethyl)hydroxyethylmethylammonium, di(stearoyloxyethyl)hydroxyethylmethylammonium, methyl($C_9$-$C_{19}$)alkyl($C_{10}$-$C_{20}$)alkylamidoethylimidazolium salts, stearamidopropyltrimethylammonium salt, stearamidopropyldimethylamine, stearamidopropyldimethylcetearylammonium salt, and mixtures thereof.

The cationic surfactant(s) may be present in a content ranging from 0.01% to 15% by weight, preferably ranging from 0.1% to 10% by weight and more preferentially ranging from 0.2% to 5% by weight, relative to the total weight of the composition of the invention.

When the composition in accordance with the invention comprises one or more cationic surfactants, the starches modified with an acid derivative/cationic surfactant(s) weight ratio generally ranges from 0.1 to 50, even more preferentially from 1 to 25 and better still from 1 to 10.

Among the silicones that may be used as conditioning agents in accordance with the present invention, mention may be made, in a non-limiting manner, of:

I. Volatile Silicones:

These silicones have a boiling point of between 60° C. and 260° C. Among the silicones of this type that are mentioned are:

(a) cyclic silicones comprising from 3 to 7, and preferably 4 to 5, silicon atoms.

These are, for example, the octamethylcyclotetrasiloxane sold under the name Volatile Silicone 7207® by the company Union Carbide, or Silbione 70045 V2® by the company Rhône-Poulenc, the decamethylcyclopentasiloxane sold under the name Volatile Silicone 7158® by the company Union Carbide or Silbione 70045 V5® by the company Rhône-Poulenc, and mixtures thereof. Mention is also made of cyclopolymers of the dimethylsiloxane/methylalkylsiloxane type, such as Silicone Volatile FZ 3109® sold by the company Union Carbide, which is a dimethylsiloxane/methyloctylsiloxane cyclopolymer;

(b) linear volatile silicones containing 2 to 9 silicon atoms and having a viscosity of less than or equal to $5 \times 10^{-6}$ m$^2$/s at 25° C.

These are, for example, the hexamethyldisiloxane sold under the name Silbione 70041 V0.65® by the company Rhône-Poulenc. This type of product is described in the article by Todd & Byers "Volatile silicone fluids for cosmetics", Cosmetics and Toiletries, Vol. 91, January 76, pages 27-32.

II. Non-Volatile Silicones:

These silicones are mainly constituted by polyalkylsiloxanes, polyarylsiloxanes, polyalkylarylsiloxanes and organomodified polysiloxanes, and also mixtures thereof. They may be in the form of oils, gums and resins.

Among the polyalkylsiloxanes, mention may be made mainly of linear polydimethylsiloxanes with a viscosity of greater than $5 \times 10^{-6}$ m$^2$/s, and preferably less than 2.6 m$^2$/s, i.e.:

containing trimethylsilyl end groups, such as, for example, and without limitation, the Silbione® oils of series 70047 that are sold by the company Rhône-Poulenc, the oil Wacker Belsil DM 60000 from Wacker, or certain Viscasil® products from the company General Electric;

containing trihydroxysilyl end groups of the 48 V® series from the company Rhône-Poulenc.

In this class of polyalkylsiloxanes, mention may also be made of the polyalkylsiloxanes sold by the company Goldschmidt under the names Abil Wax 9800® and Abil Wax 9801®, which are poly($C_{1-20}$)alkylsiloxanes.

Among the polyalkylarylsiloxanes, mention may be made of linear and/or branched polydimethylphenylsiloxanes and polydimethyldiphenylsiloxanes, with a viscosity from $10^{-5}$ to $5 \times 10^{-2}$ m$^2$/s, for instance:

the oil Rhodorsil® 763 from Rhône-Poulenc, the Silbione® oils of the 70641 series from Rhône-Poulenc, such as the oils Silbione 70641 V30® and Silbione 70641 V200®, the product DC 556® Cosmetic Grade Fluid from Dow Corning, the silicones of the PK series from Bayer, such as PK20®, the silicones of the PN and PH series from Bayer, such as the products PN 1000® and PH 1000®;

certain oils of the SF series from General Electric, such as SF 1250®, SF 1265®, SF 1154® and SF 1023®.

The silicone gums in accordance with the present invention are polydiorganosiloxanes with a high number-average molecular weight of between 200 000 and 1 000 000, used alone or as a mixture in a solvent selected from volatile silicones, polydimethylsiloxane (PDMS) oils, polyphenylmethylsiloxane (PPMS) oils, isoparaffins, methylene chloride, pentane, dodecane, tridecane and tetradecane, or mixtures thereof.

Mention is made, for example, of the compounds having the following structures:

poly[(dimethylsiloxane)/(methylvinylsiloxane)] gums,
poly[(dimethylsiloxane)/(diphenylsiloxane)] gums,
poly[(dihydrogenodimethylsiloxane)/(divinylsiloxane)] gums,
poly[(dimethylsiloxane)/(phenylmethylsiloxane)] gums,
poly[(dimethylsiloxane)/(diphenylsiloxane)/(methylvinylsiloxane)] gums.

The Mirasil DM 300 000 gum from the company Rhodia may be mentioned.

Mention may also be made, for example, in a nonlimiting manner, of the following mixtures:

1) mixtures formed from a hydroxyl-terminated polydimethylsiloxane (dimethiconol according to CTFA nomenclature) and from a cyclic polydimethylsiloxane (cyclomethicone according to CTFA nomenclature), such as the products Q2 1401® or Dow Corning 1501 Fluid sold by the company Dow Corning;

2) mixtures formed from a polydimethylsiloxane gum with a cyclic silicone, such as the product SF 1214 Silicone Fluid® from General Electric, which is an SE 30® gum of MW 500 000 (-$M_n$) dissolved in SF 1202 Silicone Fluid® (decamethylcyclopentasiloxane);

3) mixtures of two PDMSs of different viscosities, especially of a PDMS gum and a PDMS oil, such as the products SF 1236® and CF 1241® from the company General Electric. The product SF 1236® is the mixture of an SE 30® gum defined above, with a viscosity of 20 m²/s, and of an SF 96® oil with a viscosity of 5×10⁶ m²/s (15% SE 30® gum and 85% SF 96® oil).

The product CF 1241® is the mixture of an SE 30® gum (33%) and of a PDMS (67%), with a viscosity of 10⁻³ m²/s.

The organopolysiloxane resins that may be used in accordance with the invention are crosslinked siloxane systems containing the following units: $R_2SiO_{2/2}$, $RSiO_{3/2}$ and $SiO_{4/2}$ in which R represents a hydrocarbon-based group containing 1 to 6 carbon atoms or a phenyl group. Among these products, those which are particularly preferred are those in which R denotes a lower ($C_1$-$C_4$) alkyl group or a phenyl group.

Among these resins, mention may be made of the product sold under the name Dow Corning 593® or those sold under the names Silicone Fluid SS 4230 and Silicone Fluid SS 4267 by the company General Electric, which are dimethyl/trimethyl polysiloxanes.

The organomodified silicones in accordance with the present invention are silicones as defined above, comprising, in their general structure, one or more organofunctional groups directly attached to the siloxane chain or attached via a hydrocarbon-based group.

Mention may be made, for example, of the silicones comprising:

a) perfluoro groups such as trifluoroalkyls, for instance those sold by the company General Electric under the names FF.150 Fluorosilicone Fluid® or by the company Shin-Etsu under the names X-22-819®, X-22-82®, X-22-821® and X-22-822®;

b) hydroxyacylamino groups, for instance those described in Patent Application EP 0 342 834 and in particular the silicone sold by the company Dow Corning under the name Q2-8413®;

c) thiol groups, as in the silicones X 2-8360® from the company Dow Corning or GP 72A® and GP 71® from Genesee;

d) non-quaternized amine groups, such as GP 4 Silicone Fluid® from Genesee, GP 7100® from Genesee, Q2 8220® from Dow Corning, AFL 40® from Union Carbide or the silicone known as Amodimethicone in the CTFA dictionary;

e) carboxylate groups, for instance the products described in Patent EP 186 507 from Chisso Corporation;

f) hydroxylated groups, for instance the polyorganosiloxanes containing a hydroxyalkyl function, described in French Patent Application FR 8 516 334.

Mention may be made most particularly of the product sold by Dow Corning under the name DC 190;

g) alkoxylated groups, as in the silicone copolymer F 755® from SWS Silicones and the products Abil Wax 2428®, Abil Wax 2434® and Abil Wax 2440® from the company Goldschmidt;

h) acyloxyalkyl groups, for instance the polyorganopolysiloxanes described in Patent Application FR 8 817 433, corresponding to formula (XXIV) below:

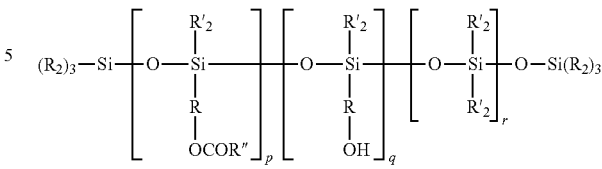

(XXIV)

in which:

$R_2$ denotes methyl, phenyl, OCR" or hydroxyl, but only one $R_2$ per silicon atom may be OH;

$R'_2$ denotes methyl or phenyl, at least 60 mol % of the entirety of the $R_2$ and $R'_2$ groups being methyl;

R" denotes $C_8$-$C_{20}$ alkyl or alkenyl;

R denotes a linear or branched, divalent $C_2$-$C_{18}$ hydrocarbon-based alkylene;

r is between 1 and 120 inclusive;

p, q is 0 or is less than 0.5 p, with p+q being between 1 and 30 inclusive:

the polyorganosiloxanes of formula (XXIV) may contain groups:

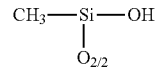

in proportions not exceeding 15% of the sum p+q+r;

i) quaternary ammonium groups, as in the products X2 81 08® and X2 81 09® and the product Abil K 3270® from the company Goldschmidt;

j) amphoteric or betaine groups, such as in the product sold by the company Goldschmidt under the name Abil B 9950®;

k) bisulfite groups, for instance in the products sold by the company Goldschmidt under the names Abil S 201® and Abil S 255®;

l) polyethyleneoxy and/or polypropyleneoxy groups optionally comprising $C_6$-$C_{24}$ alkyl groups, such as the products called dimethicone copolyol sold by the company Dow Corning under the name DC 1248, or the oils Silwet L 722, L 7500, L 77 and L 711 from the company Union Carbide, and the alkyl ($C_{12}$) methicone copolyol sold by the company Dow Corning under the name Q2 5200.

According to the invention, it is also possible to use silicones comprising a polysiloxane portion and a portion composed of a non-silicone organic chain, with one of the two portions making up the main chain of the polymer and the other being grafted onto said main chain. These polymers are described, for example, in Patent Applications EP-A-412 704, EP-A-412 707, EP-A-640 105 and WO 95/00578, EP-A-582 152 and WO 93/23009 and U.S. Pat. No. 4,693,935, U.S. Pat. No. 4,728,571 and U.S. Pat. No. 4,972,037. These polymers are preferably anionic or non-ionic.

Such polymers are, for example, copolymers that may be obtained by free-radical polymerization from the monomer mixture formed from:

a) 50% to 90% by weight of tert-butyl acrylate;

b) 0 to 40% by weight of acrylic acid;

c) 5% to 40% by weight of silicone macromer of formula (XXV):

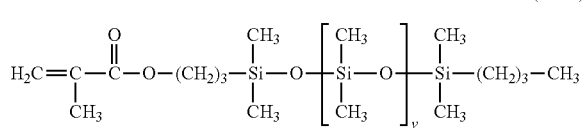
(XXV)

where v is a number ranging from 5 to 700; the percentages by weight being calculated relative to the total weight of the monomers.

Other examples of grafted silicone polymers are, in particular, polydimethylsiloxanes (PDMSs) onto which are grafted, by means of a connecting link of thiopropylene type, mixed polymer units of the poly((meth)acrylic acid) type and of the poly(alkyl (meth)acrylate) type; and polydimethylsiloxanes (PDMSs) onto which are grafted, by means of a connecting link of thiopropylene type, polymer units of the poly(isobutyl (meth)acrylate) type.

According to the invention, all the silicones can also be used in the form of emulsions, nanoemulsions or microemulsions.

The particularly preferred polyorganosiloxanes in accordance with the invention are:
  non-volatile silicones selected from the family of polyalkylsiloxanes with trimethylsilyl end groups, such as oils having a viscosity of between 0.2 and 2.5 m²/s at 25° C., for instance the oils of the DC200 series from Dow Corning, in particular the one with a viscosity of 60 000 cSt, or of the Silbione 70047 and 47 series, and more particularly the oil 70 047 V 500 000 sold by the company Rhodia Chimie, and polyalkylsiloxanes with dimethylsilanol end groups, such as dimethiconols, or polyalkylarylsiloxanes, for instance the oil Silbione 70641 V 200 sold by the company Rhodia Chimie;
  polysiloxanes containing amino groups, such as amodimethicones or trimethylsilylamodimethicones.

The viscosities of the silicones may especially be determined by the standard ASTM D445-97 (viscometry).

When the conditioning agent of the composition according to the invention is a hydrocarbon, it is a linear or branched $C_8$-$C_{30}$ hydrocarbon.

Among the hydrocarbons that are liquid at room temperature corresponding to this definition, mention may be made especially of isododecane, isohexadecane and isomers thereof (such as 2,2,4,4,6,6-heptamethylnonane), isoeicosane, isotetracosane, isomers of the said compounds, n-nonadecane, n-dodecane, n-undecane, n-tridecane and n-pentadecane, liquid petroleum jelly, and mixtures of these hydrocarbons.

Use is preferably made according to the invention of isododecane or an isomer thereof, or liquid petroleum jelly.

When the conditioning agent is a fatty alcohol, this alcohol is a linear or branched, saturated or unsaturated $C_8$-$C_{30}$ alcohol. Among the latter, mention may, for example, be made of 2-butyloctanol, lauryl alcohol, 2-octyldodecanol, oleyl alcohol, isocetyl alcohol, isostearyl alcohol, stearyl alcohol, cetyl alcohol and behenyl alcohol, and mixtures thereof.

When the conditioning agent is a fatty ester, this ester may be either an ester of a $C_8$-$C_{30}$ fatty acid and a $C_1$-$C_{30}$ alcohol, and especially an ester of a $C_8$-$C_{30}$ fatty acid and a $C_8$-$C_{30}$ fatty alcohol, or an ester of a $C_1$-$C_7$ acid or diacid and a $C_8$-$C_{30}$ fatty alcohol.

Among these esters, mention may, for example, be made of ethyl, isopropyl, 2-ethylhexyl and 2-octyldecyl palmitate, isopropyl, butyl, cetyl and 2-octyldecyl myristate, butyl and hexyl stearate, hexyl and 2-hexyldecyl laurate, isononyl isononanoate, dioctyl malate, myristyl myristate, cetyl palmitate, and mixtures thereof.

This ester may also be an ester of a polyol and especially of glycerol, such as a natural or synthetic glyceride. Natural triglycerides that may be mentioned include plant oils such as avocado oil, olive oil, wheatgerm oil, sunflower oil, argan oil, corn oil, soybean oil, marrow oil, grapeseed oil, sesame seed oil, hazelnut oil, apricot oil, macadamia oil, arara oil, castor oil, rapeseed oil, coconut oil, sweet almond oil, safflower oil, candlenut oil, camellina oil, tamanu oil, babassu oil and pracaxi oil, and mixtures thereof.

The ceramides or ceramide analogues, such as glycoceramides, that may be used as conditioning agent in the compositions according to the invention are known per se and are natural or synthetic molecules that may correspond to the general formula (XXVI) below:

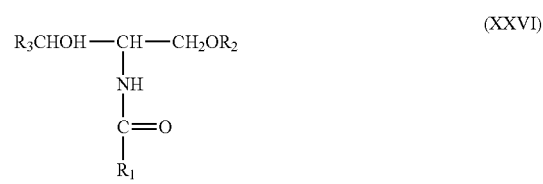
(XXVI)

in which:
  $R_1$ denotes a linear or branched, saturated or unsaturated alkyl group, derived from $C_{14}$-$C_{30}$ fatty acids, it being possible for this group to be substituted with a hydroxyl group in the alpha position, or a hydroxyl group in the omega position esterified with a saturated or unsaturated $C_{16}$-$C_{30}$ fatty acid;
  $R_2$ denotes a hydrogen atom or a (glycosyl)$_n$, (galactosyl)$_m$ or sulfogalactosyl group, in which n is an integer ranging from 1 to 4 and m is an integer ranging from 1 to 8;
  $R_3$ denotes a $C_{15}$-$C_{26}$ hydrocarbon-based group which is saturated or unsaturated in the alpha position, it being possible for this group to be substituted with one or more $C_1$-$C_{14}$ alkyl groups;
  it being understood that, in the case of natural ceramides or glycoceramides, $R_3$ can also denote a $C_{15}$-$C_{26}$ α-hydroxyalkyl group, the hydroxyl group being optionally esterified with a $C_{16}$-$C_{30}$ α-hydroxy acid.

The ceramides which are preferred in the context of the present invention are those described by Downing in Arch. Dermatol., Vol. 123, 1381-1384, 1987, or those described in French Patent FR 2 673 179.

The ceramide(s) that are more particularly preferred according to the invention are the compounds for which $R_1$ denotes a saturated or unsaturated alkyl derived from $C_{16}$-$C_{22}$ fatty acids; $R_2$ denotes a hydrogen atom; and $R_3$ denotes a saturated linear $C_{15}$ group.

Such compounds are, for example:
N-linoleyldihydrosphingosine,
N-oleyldihydrosphingosine,
N-palmitoyldihydrosphingosine,
N-stearoyldihydrosphingosine,
N-behenyldihydrosphingosine,
  or mixtures of these compounds.

Even more preferentially, ceramides are used for which $R_1$ denotes a saturated or unsaturated alkyl group derived from fatty acids; $R_2$ denotes a galactosyl or sulfogalactosyl group; and $R_3$ denotes a —CH═CH—$(CH_2)_{12}$—$CH_3$ group.

Among all of these conditioning agents, preference is given to the use of one or more conditioning agents selected from silicones such as organosiloxanes and cationic polymers.

The composition according to the invention preferably contains from 0.01% to 20% by weight, and more preferably from 0.05% to 10% by weight of conditioning agent(s), relative to the total weight of the composition.

The composition according to the invention may also comprise one or more conventional additives that are well known in the art, other than the compounds defined previously. As examples of additives that may be used according to the invention, mention may be made of anionic surfactants, amphoteric or zwitterionic surfactants, nonionic surfactants, proteins, protein hydrolysates, vitamins, reducing agents, plasticizers, softeners, antifoams, moisturizers, pigments, clays, mineral fillers, UV-screening agents, abrasive agents (pumice, apricot kernel powder), mineral colloids, peptizers, solubilizers, fragrances, preservatives, nacreous agents, propellants, antidandruff agents (for example, zinc pyrithione, octopirox, selenium sulfide, ellagic acid and derivatives), agents for combating hair loss or agents for promoting hair regrowth; these additives being other than the compounds defined above.

A person skilled in the art will take care to select the optional additive(s) and the amount thereof such that they do not harm the properties of the compositions of the present invention.

The additive(s) are generally present in the composition according to the invention in an amount ranging from 0 to 20% by weight relative to the total weight of the composition.

The compositions according to the invention may be provided in all the formulation forms conventionally used for a topical application and in particular in the form of aqueous or aqueous/alcoholic solutions, of oil-in-water (O/W), water-in-oil (W/O) or multiple (triple: W/O/W or O/W/O) emulsions, of aqueous gels or of dispersions of a fatty phase in an aqueous phase using spherules, it being possible for these spherules to be polymeric nanoparticles, such as nanospheres and nanocapsules, or lipid vesicles of ionic and/or nonionic type (liposomes, niosomes or oleosomes). These compositions are prepared according to the usual methods.

In addition, the compositions used according to the invention can be more or less fluid and can have the appearance of a white or coloured cream, of an ointment, of a milk, of a lotion, of a serum, of a paste or of a foam. They can optionally be applied to the keratin materials in aerosol form. They can also be in solid form, for example in the form of a stick.

Of course, the person skilled in the art will take care to choose the optional compound or compounds to be added to the composition according to the invention so that the advantageous properties intrinsically attached to the composition in accordance with the invention are not, or not substantially, adversely affected by the envisaged addition or additions.

As indicated above, a further subject of the invention is a method for the nontherapeutic cosmetic treatment of keratin materials, in particular the hair, comprising the application, to said materials, of a composition as described above.

This application may or may not be followed by rinsing.

When the application of the composition is followed by a rinsing operation, the leave-in time of the composition on the keratin materials ranges from a few seconds to 60 minutes, better still from 5 seconds to 30 minutes, even better still from 10 seconds to 10 minutes.

Whether in rinsed mode or non-rinsed mode, the application of the composition may take place in the presence of heat. The heating device may be a hairdryer, a hood dryer, a curling iron or a flat iron. The heating temperature may be between 40° C. and 220° C.

The application of the composition according to the invention to the hair may take place on dry hair or on wet hair. It may in particular be carried out after a shampooing operation or after a pretreatment at acidic or basic pH.

A subject of the invention is also the use of a composition according to the invention for caring for and/or shaping keratin materials, especially keratin fibres and in particular human keratin fibres such as the hair.

The examples that follow are intended to illustrate the invention without, however, being limiting in nature.

EXAMPLE 1

The rinse-out care composition (A) is prepared from the ingredients indicated in the table below, the amounts of which are expressed as weight percentages of active material relative to the total weight of the composition.

| Composition | A (invention) |
|---|---|
| 3-Aminopropyltriethoxysilane | 1 |
| Potato starch acetate (Perfectamyl AC from Avebe) | 1 |
| Hydroxyethylcellulose (Natrosol 250 HHR from Ashland) | 0.2 |
| C16/C18 cetylstearyl alcohol (50/50) | 3.5 |
| Mixture of myristyl myristate, cetyl palmitate and stearyl stearate (Miraceti from Laserson) | 0.7 |
| Behenyltrimethylammonium chloride as a 79% solution in isopropanol (Genamin KDMP from Clariant) | 1.58 |
| Lactic acid qs | pH 9 |
| Fragrance qs | |
| Chlorhexidine digluconate | 0.2 |
| Water | qs 100% |

When applied as a rinse-out hair conditioner, composition (A) gives the hair mass, volume and also a uniform feel from the root to the end.

Furthermore, this composition makes it possible to facilitate the shaping of fine hair and to give a better curl definition to curly hair.

EXAMPLE 2

Composition (B) is prepared from the ingredients indicated in the table below, the amounts of which are expressed as weight percentages of active material relative to the total weight of the composition.

| Composition | B (invention) |
|---|---|
| 3-Aminopropyltriethoxysilane | 5 |
| Hydroxypropyl corn starch phosphate (Structure ZEA from Akzo Nobel) | 4.4 |

-continued

| Composition | B (invention) |
|---|---|
| Hydroxyethylcellulose (Natrosol 250 HHR from Ashland) | 0.7 |
| Lactic acid | 1.75 |
| pH agent qs | pH 9 |
| Deionized water | qs 100% |

Composition (C) is prepared from the ingredients indicated in the table below, the amounts of which are expressed as weight percentages of active material relative to the total weight of the composition.

| Composition | C |
|---|---|
| Bis(diglyceryl) poly(2-acyladipate) (Softisan 649 from Sasol) | 0.15 |
| Amino silicone in an aqueous emulsion containing 60% AM (Dow Corning 2-8299 Cationic Emulsion from Dow Corning) | 0.96 |
| Hydroxyethylcellulose (Natrosol 250 HHR from Ashland) | 0.2 |
| C16/C18 cetylstearyl alcohol (50/50) | 3 |
| Mixture of myristyl myristate, cetyl palmitate and stearyl stearate (Miraceti from Laserson) | 0.25 |
| Lauryl PEG/PPG-18/18 methicone at 72% active material (Dow Corning 5200 Formulation Aid - Dow Corning) | 0.18 |
| Behenyltrimethylammonium chloride as a 79% solution in isopropanol (Genamin KDMP from Clariant) | 1.58 |
| pH agent qs | pH 3.5 |
| PEG-180 (Polyethylene glycol) | 2 |
| L-Glycine | 0.01 |
| D-Panthenol | 0.1 |
| Vitamin E acetate | 0.1 |
| 2-Oleamido-1,3-octadecanediol | 0.01 |
| Fragrance qs | |
| Preserving agents, dyes | qs |
| Water | qs 100% |

Compositions B and C are conditioned in a two-bodied device consisting of two compartments and of a dispensing head for dispensing a mixture consisting of equal amounts of compositions B and C.

When applied as a rinse-out hair conditioner, the mixture of compositions (B) and (C) (50/50 by weight) gives the hair mass, volume and also a uniform feel from the root to the end.

Furthermore, this composition makes it possible to facilitate the shaping of fine hair and to give a better curl definition to curly hair.

The invention claimed is:

1. A rinse-out hair conditioner composition comprising:
   (i) 3-aminopropyltriethoxysilane in an amount ranging from about 0.2% to about 5% by weight, relative to the total weight of the composition, and
   (ii) potato starch acetate in an amount ranging from about 0.5% to about 5% by weight, relative to the total weight of the composition.

2. A process for the nontherapeutic treatment of keratin fibers, comprising:
   applying to said keratin fibers a rinse-out hair conditioner composition comprising:
   (i) 3-aminopropyltriethoxysilane in an amount ranging from about 0.2% to about 5% by weight, relative to the total weight of the composition; and
   (ii) potato starch acetate in an amount ranging from about 0.5% to about 5% by weight, relative to the total weight of the composition; and
   rinsing the composition from the keratin fibers after applying the composition to the keratin fibers.

3. A process for shaping human hair, comprising:
   applying to said human hair a rinse-out hair conditioner composition comprising:
   (i) 3-aminopropyltriethoxysilane in an amount ranging from about 0.2% to about 5% by weight, relative to the total weight of the composition, and
   (ii) potato starch acetate in an amount ranging from about 0.5% to about 5% by weight, relative to the total weight of the composition; and
   rinsing the composition from the keratin fibers after applying the composition to the keratin fibers.

* * * * *